(12) United States Patent
Yeh et al.

(10) Patent No.: US 10,118,023 B2
(45) Date of Patent: Nov. 6, 2018

(54) CLOSED-SYSTEM CATHETER ASSEMBLY

(71) Applicant: CareFusion 303, Inc., San Diego, CA (US)

(72) Inventors: Jonathan Yeh, Diamond Bar, CA (US); George Mansour, Pomona, CA (US); Chris Zollinger, Chino Hills, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 15/164,826

(22) Filed: May 25, 2016

(65) Prior Publication Data

US 2016/0271369 A1   Sep. 22, 2016

Related U.S. Application Data

(63) Continuation of application No. 13/673,975, filed on Nov. 9, 2012, now Pat. No. 9,352,127.

(51) Int. Cl.
*A61M 5/178* (2006.01)
*A61M 25/06* (2006.01)

(52) U.S. Cl.
CPC .... *A61M 25/0606* (2013.01); *A61M 25/0631* (2013.01); *A61M 25/0693* (2013.01)

(58) Field of Classification Search
CPC .......... A61M 25/0606; A61M 25/0693; A61M 25/0631
See application file for complete search history.

(56) References Cited

U.S. PATENT DOCUMENTS

| | | | |
|---|---|---|---|
| 5,215,525 A | 6/1993 | Sturman | |
| 5,885,251 A | 3/1999 | Luther | |
| 6,547,762 B1 | 4/2003 | Botich et al. | |
| 2010/0204648 A1 | 8/2010 | Stout et al. | |
| 2012/0016307 A1* | 1/2012 | Burkholz | A61B 5/1422 604/168.01 |
| 2013/0079720 A1* | 3/2013 | Finnestad | A61M 25/0618 604/164.08 |

(Continued)

FOREIGN PATENT DOCUMENTS

| | | |
|---|---|---|
| CN | 1285758 A | 2/2001 |
| CN | 1319023 A | 10/2001 |
| CN | 102355923 A | 2/2012 |

(Continued)

OTHER PUBLICATIONS

Australian Examination Report No. 1 for Application No. 2013341542, dated Jul. 17, 2017, 3 pages.

(Continued)

*Primary Examiner* — Rebecca E Eisenberg
(74) *Attorney, Agent, or Firm* — McDermott Will & Emery LLP

(57) ABSTRACT

A catheter system including an insertion device and a catheter device. The insertion device includes a housing, a latch, a needle for insertion into a patient; and a spring. The catheter device includes a housing comprising a chamber, and a seal disposed in said chamber. The seal is configured to reseal when the needle is withdrawn from the seal such that blood is sealed in the chamber. The spring relaxes and thereby retracts the needle entirely into the housing of the insertion device when the latch decouples from the catheter device.

17 Claims, 7 Drawing Sheets

(56) References Cited

U.S. PATENT DOCUMENTS

2015/0165165 A1\* 6/2015 Rodriguez Lelis ............... A61M 25/0631
600/576

FOREIGN PATENT DOCUMENTS

| EP | 812602 A2 | 12/1997 |
|---|---|---|
| JP | H10108910 A | 4/1998 |
| JP | 2001522658 A | 11/2001 |
| JP | 2002521143 A | 7/2002 |
| JP | 2010526591 A | 8/2010 |
| JP | 2012517326 A | 8/2012 |
| WO | WO-2012/009459 A1 | 1/2012 |
| WO | WO-2012/106266 A1 | 8/2012 |

OTHER PUBLICATIONS

Japanese Office Action for Application No. 2015-541824, dated Aug. 3, 2017, 4 pages excluding translation.
International Search Report and Written Opinion for Application No. PCT/US2013/068151, dated May 12, 2014.
International Preliminary Report on Patentability for Application No. PCT/US2013/068151, dated Nov. 24, 2014, 5 pages.
European Office Action for Application No. 13792167.2, dated Jun. 7, 2016, 3 pages.
Japanese Office Action for Application No. 2015-541824, dated Feb. 15, 2018, 4 pages excluding English translation.
Chinese Office Action for Application No. 201380064233.1, dated Nov. 6, 2017, 6 pages excluding translation.
Japanese Patent Application No. 2015541824, dated Jul. 10, 2018, 9 pages.

\* cited by examiner

CLOSED-SYSTEM CATHETER ASSEMBLY

CROSS-REFERENCE TO RELATED APPLICATIONS

The present application claims the benefit of priority under 35 U.S.C. § 120 as a continuation of U.S. patent application Ser. No. 13/673,975 entitled "Closed-System Catheter Assembly," filed on Nov. 9, 2012, the disclosure of which is hereby incorporated by reference in its entirety for all purposes.

BACKGROUND

Typically, may be difficult to couple a catheter to extension devices while also preventing blood leakage.

The drawings referred to in this description should fee understood as not being drawn to scale except if specifically noted.

BRIEF DESCRIPTION

Reference will now be made in detail to embodiments of the present technology, examples of which are illustrated in the accompanying drawings. While the technology will be described in conjunction with various embodiments), it will be understood that they are not intended to limit the present technology to these embodiments. On the contrary, the present technology is intended to coyer alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, and components have not been described in detail as not to unnecessarily obscure aspects of the present embodiments.

Figure 1:
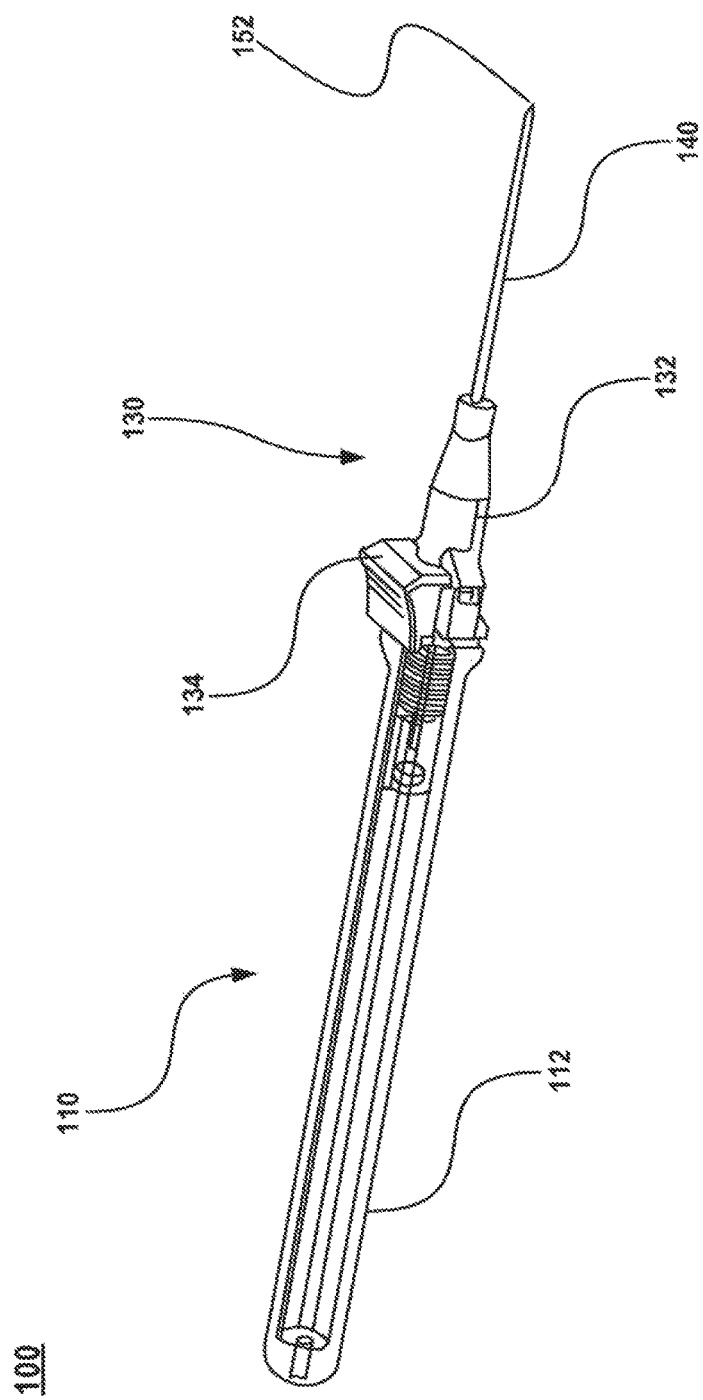
FIGS. 1-6B illustrates embodiments of various catheter systems in various states.
Figure 2:
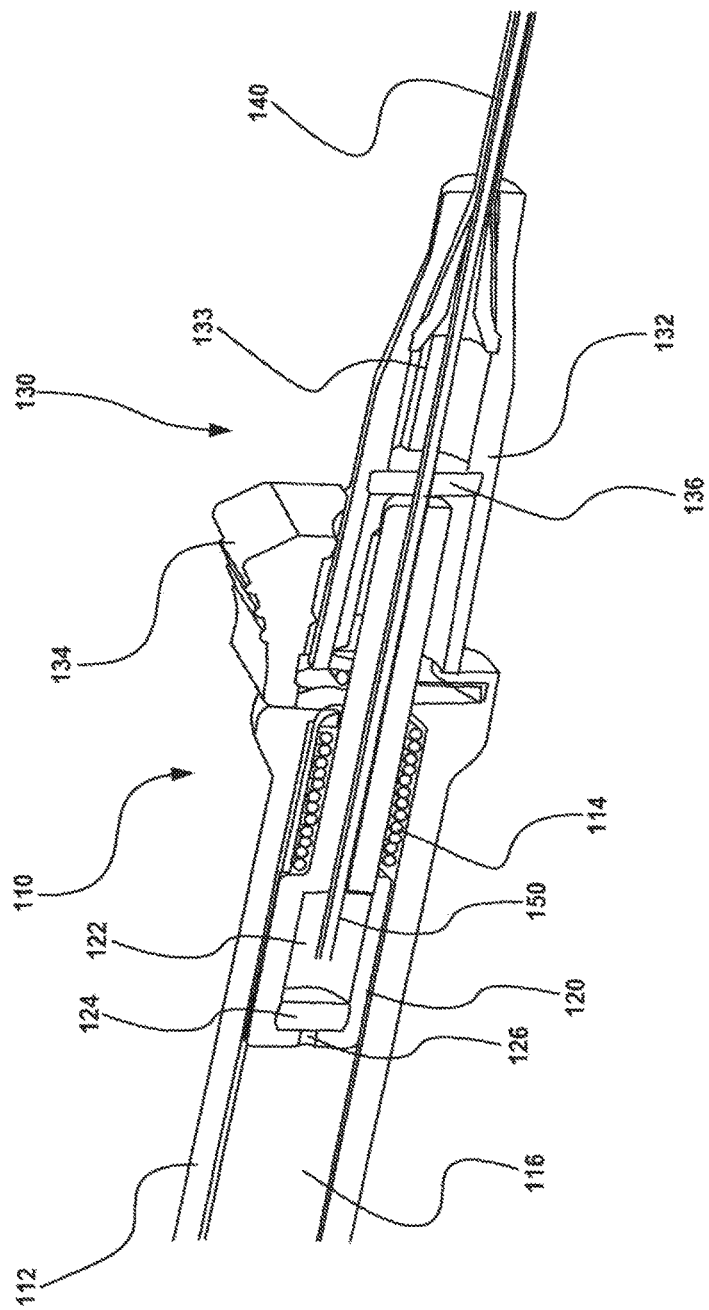

FIG. 1 depicts an embodiment of catheter system 100 (or catheter assembly) in a pre-insertion state. FIG. 2 depicts a cross-sectional view of the catheter system 100 in the pre-insertion state. A pre-insertion state is the state of catheter system 100 prior to inserting the catheter into a patient.

Catheter system 100 includes catheter insertion device 110 coupled to catheter device 130. Catheter insertion device 110 is resiliency coupled to catheter device 130 via latch 134. In one embodiment, latch 134 is a spring latch that flexibly and resiliency engages (e.g., snap fit) with any physical features (e.g., protrusions, indentions, etc.) on housing 132 of catheter device 130. It should be appreciated that catheter insertion device 110 is coupled to catheter device 130 without requiring a threaded coupling.

In contrast, conventional catheter systems a catheter device is coupled to an insertion device via threads. As such, the insertion device must be rotated to couple/decouple it from the catheter device.

In one embodiment, latch 134 resiliently couples to internal features of catheter device 130. In another embodiment, latch 134 is rotatable with respect to catheter device 130 when resiliently coupled to catheter device 130.

Needle 150 is held by needle collet 120. An end of needle 150 is disposed in viewing chamber 122. When in the pre-insertion state, needle 150 extends through and out of catheter device 130 and is also disposed within catheter 140.

Moreover, in the pre-insertion state, spring 114 is compressed and abuts against needle collet 120.

During insertion, needle 150 and catheter 140 are inserted into a vein of a patient. When properly inserted, blood travels within needle 150 to viewing chamber 122. In particular, the blood does not come into contact with any internal surface of (e.g., chamber 133) of catheter device 130 when catheter insertion device 110 is coupled to catheter device 130.

When blood is provided in viewing chamber 122, the blood is able to be viewed through housing 112 and needle collet 120 to provide a visual indication that needle 150 and catheter 140 have been properly inserted into the vein. As such, both housing 112 and needle collet 120 are either translucent or transparent.

The blood is sealed in viewing chamber by filter 124. In one embodiment, filter 124 is a hydrophobic filter. In particular, when blood enters into viewing chamber 122, air passes through filter 124 and exits vent 126 into ambient. However, the blood is not able to pass through filter 124.

In order to withdraw needle 150 from the vein, catheter insertion device 110 is withdrawn from catheter device 130. However, latch 134 still remains in contact with and is coupled to catheter device 130 via features on housing 132. During withdrawal, needle 150 is also withdrawn through catheter 140 (which remains in the vein).

Figure 3:
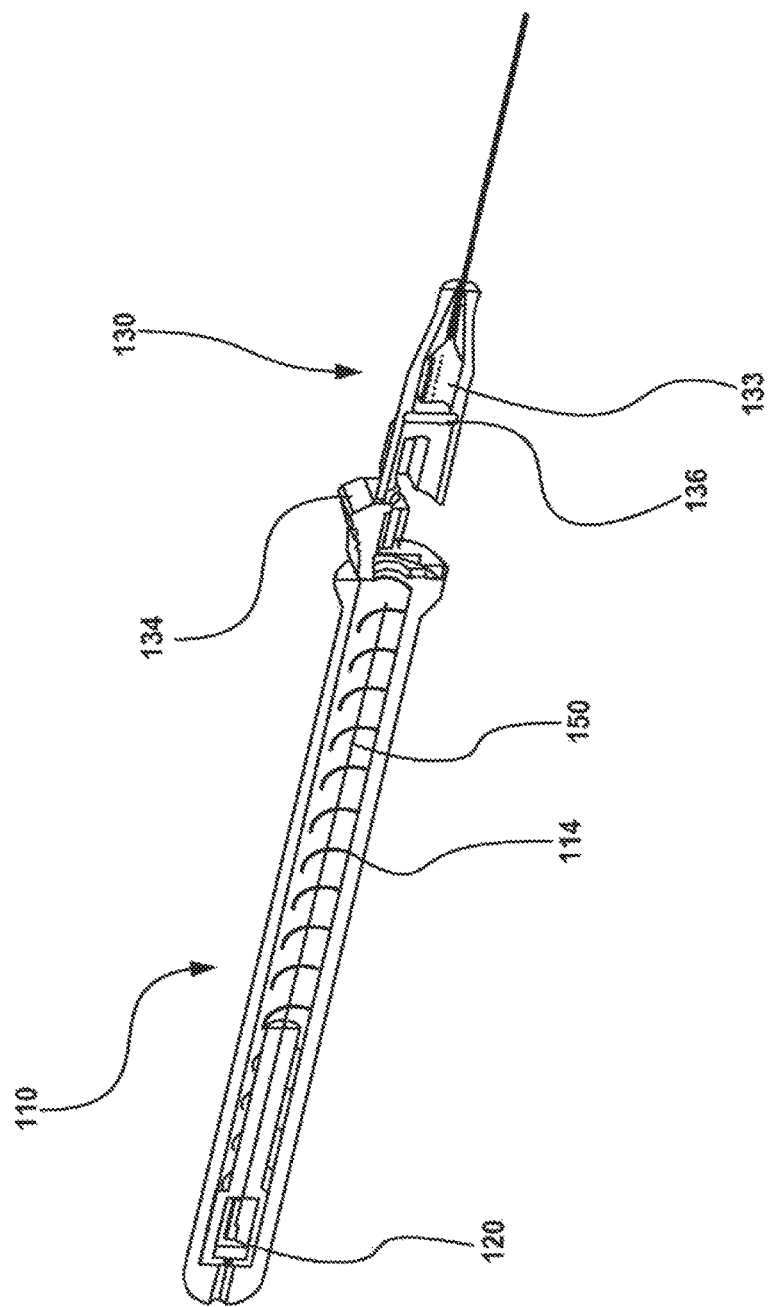

Once latch 134 is completely decoupled from catheter device 130 (e.g., latch 134 does not engage with retaining features on housing 132), spring 114 is released info its relaxed state. In doing so, spring 114 urges needle collet 120 such that it axially slides within chamber 116. As a result, needle 150 is completely withdrawn through catheter device 130 and is entirely disposed within housing 112, as depicted in FIG. 3. In other words, needle 150 is automatically withdrawn from the vein and through catheter device 130 when latch 134 is decoupled from housing 132. When no longer coupled to catheter device 130, catheter insertion device 110 may be properly discarded.

Once needle 150 is withdrawn through seal 136, seal 136 reseals. As such, blood entering into chamber 133, via catheter 140 is sealed within chamber 133 to prevent blood loss. Therefore, catheter device 130 is also a closed system because blood is securely sealed within chamber 133. In one embodiment seal 136 is a silicone disc. In another embodiment, seal 136 is pre-slit to facilitate in the insertion/withdrawal of device (e.g., needle 150).

Figure 4:
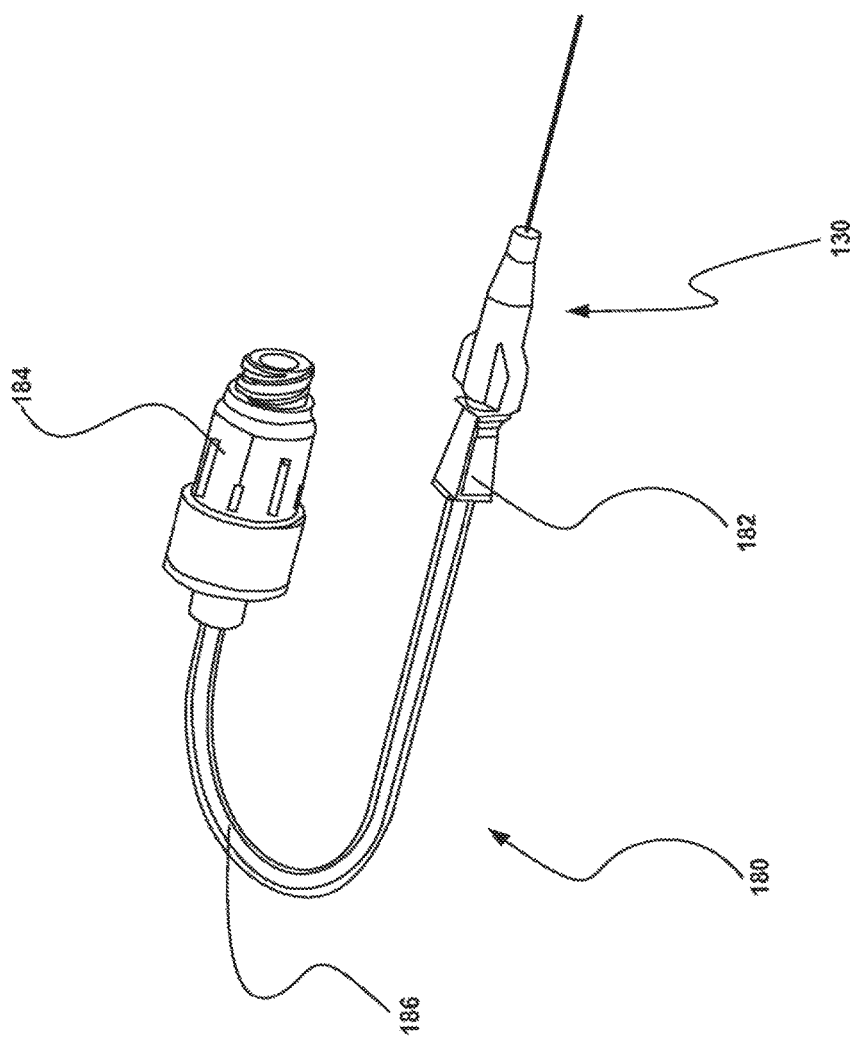
Figure 5:
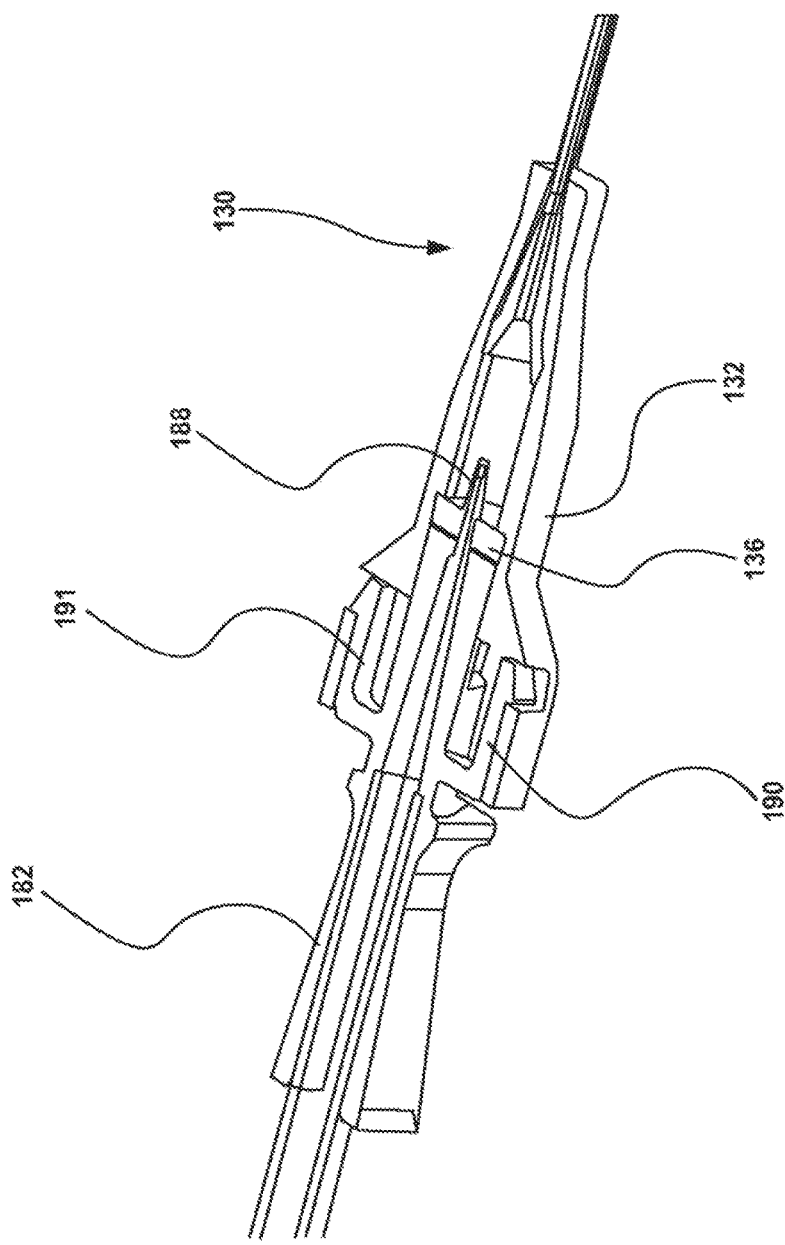

FIG. 4 depicts an embodiment of extension set 180 coupled to catheter device 130. FIG. 5 depicts a cross-sectional view of extension set 180 coupled to catheter device 130.

In order to couple extension set 180 to catheter device 130, a user grasps base 132 an inserts cannula 188 through seal 136 until coupling features 190 and 191 (e.g., tines) mechanically couple (e.g., snap fit) with associated coupling features of housing 132. The coupling may be provided by use of a single hand of a user.

In contrast, in conventional systems, the extension set is rotatably coupled to the catheter via treads. Moreover, a user must use both hands to couple the catheter to the extension set. For example, a user must hold onto the catheter and use the other hand to handle the extension set and rotated with respect to the catheter.

When properly coupled, blood is able to flow through tube 186 to luer access device 184. It should be appreciated that any compatible disposable set or extension set may be coupled to catheter device 130.

Figure 6A:
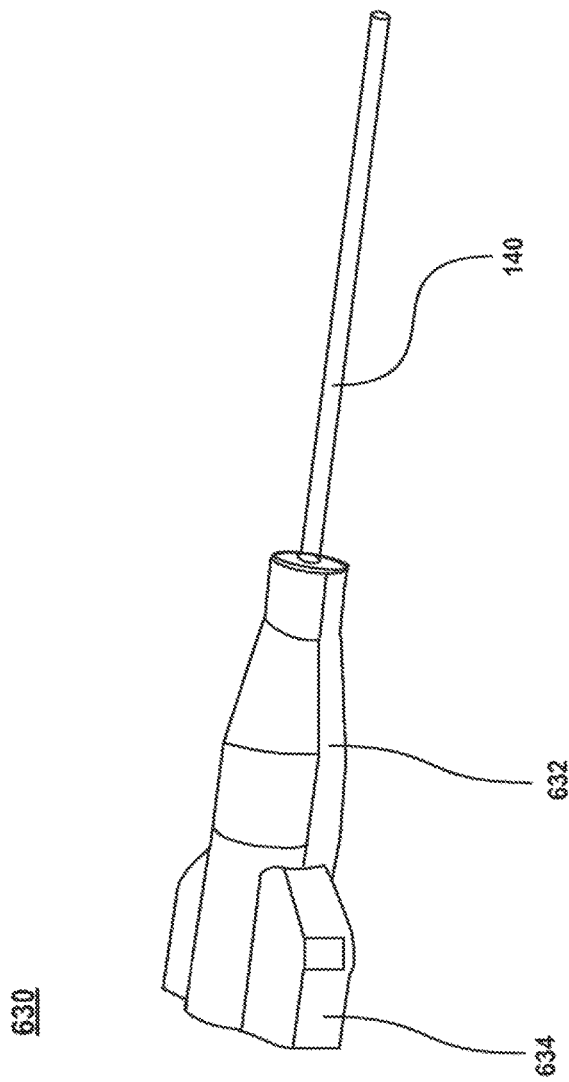
Figure 6B:
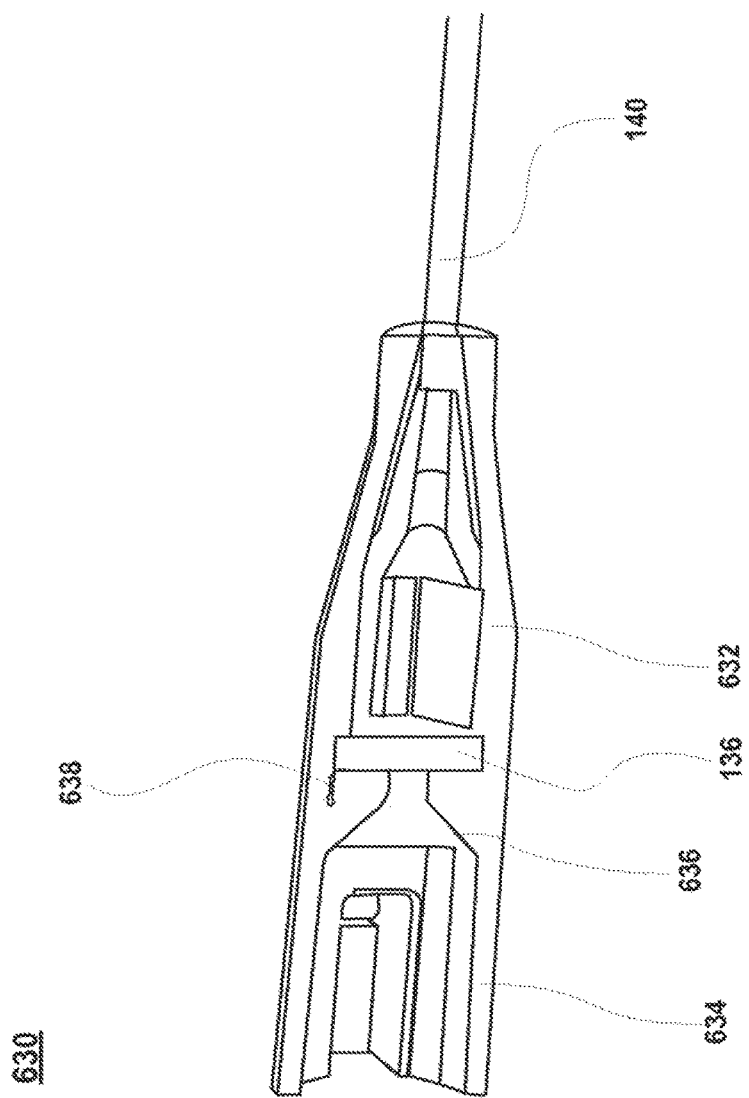

FIGS. 6A-B depict an embodiment of catheter device 630. Catheter device 630 includes first section 632 that is joined to second section 634. The joining can be but is not limited to an ultrasonic weld, adhesive, snap fit, etc. Seal 136 is placed between first section 632 and second section 634 prior to joining and is securely seated between first section 632 and second section 634 when the sections are joined at joint 638.

In one embodiment, second section 634 includes funnel 636 to facilitate in the guiding of needle 150 through catheter device 630 during assembly such that needle 150 is properly aligned to puncture seal 136.

It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:
1. A catheter system comprising:
an insertion device comprising:
a housing;
a latch, coupled to and extending from said housing, said latch comprising an external portion and an internal portion;
a needle slidably disposed within said housing;
a spring; and
a catheter device, said catheter device comprising:
a housing comprising a portion configured to engage with said external portion of said latch of said insertion device, wherein:
said latch comprises a first position in which said internal portion of said latch prevents extension of said spring and a second position in which said internal portion is configured to release said spring to extend such that said spring relaxes and thereby retracts said needle entirely into said housing of said insertion device, and wherein said latch is configured to be held in said first position by an engagement of said external portion with said portion of said housing of said catheter device and to be released to said second position when said external portion of said latch is configured to decouple from said catheter device, and
said catheter device further comprises a chamber and a seal disposed within said chamber, wherein said seal is configured to be punctured by an extension set such that blood is able to exit said chamber into said extension set.

2. The catheter system of claim 1, wherein said spring is compressed when said catheter device is coupled to said insertion device and said latch is in said first position.

3. The catheter system of claim 1, wherein said insertion device is configured such that blood passes through said catheter device via said needle into a viewing chamber disposed in said insertion device.

4. The catheter system of claim 3, wherein said insertion device further comprises a needle collet coupled to said needle, and wherein said viewing chamber is disposed within said needle collet.

5. The catheter system of claim 4, wherein said needle collet is axially slidably disposed in said housing of said insertion device, and wherein said spring is configured to urge said needle collet to slide within said housing away from said latch, upon release of said latch to said second position.

6. The catheter system of claim 1, wherein said needle is configured to extend through said seal when said latch is in said first position and wherein said seal is configured to reseal when said needle is withdrawn from said seal such that blood in said chamber is sealed therein.

7. The catheter system of claim 1, further comprising said extension set, wherein said extension set is configured to snap fit to said catheter device.

8. A method, comprising:
providing a catheter system, the catheter system comprising:
an insertion device comprising:
a needle held by a needle collet,
a spring, wherein said spring is compressed and abuts against said needle collet, and
a latch comprising an internal portion that prevents extension of said spring, and an external portion, and
a catheter device, wherein said needle of said insertion device extends through and out of said catheter device and is at least partially disposed within a catheter of said catheter device, and wherein said external portion of said latch is engaged with a housing of said catheter device; and
inserting said needle and said catheter into a vein of a patient, wherein:
the catheter device further comprises a chamber and a seal,
prior to said insertion, said needle extends through said seal and through said chamber, and
when said needle is withdrawn through said catheter device entirely into said insertion device, the seal is configured to reseal so that blood entering into said chamber from said vein via said catheter is sealed within said chamber to prevent blood loss.

9. The method of claim 8, further comprising:
withdrawing said insertion device from said catheter device without rotating said insertion device relative to said catheter device to withdraw said needle from said vein and into said catheter while said external portion of said latch remains engaged with said housing of said catheter device and said internal portion of said latch prevents extension of said spring and while said catheter remains at least partially within said vein.

10. The method of claim 9, further comprising:
decoupling said external portion of said latch from said housing of said catheter device such that said internal portion of said latch is configured to release said spring to urge said needle collet to axially slide within said insertion device to completely withdraw said needle through said catheter device and entirely into said insertion device.

11. The method of claim 8, wherein, following said inserting and prior to a withdrawal, blood travels within said needle to a viewing chamber disposed in said needle collet.

12. The method of claim 11, wherein said blood travels within said needle to said viewing chamber without contacting any internal surface of said chamber of said catheter device.

13. The method of claim 12, wherein, when blood enters into said viewing chamber, air from said viewing chamber passes through a filter therein and exits said viewing chamber via a vent into ambient.

14. The method of claim 10, further comprising snap fitting an extension set to said catheter device following said decoupling.

15. A method, comprising:
    inserting a catheter of a catheter device into a vein of a patient using a needle of a catheter insertion device that is coupled to said catheter device;
    withdrawing said needle from said catheter by decoupling said catheter insertion device from said catheter device without rotating said catheter insertion device relative to said catheter device; and
    coupling an extension set to said catheter device while said catheter is disposed within said vein without rotating said extension set relative to said catheter device, wherein said coupling comprises inserting a cannula of said extension set through a seal of said catheter device until at least one coupling feature of said extension set mechanically couples with at least one associated coupling feature of a housing of said catheter device.

16. The method of claim 15, wherein said at least one coupling feature of said extension set comprises a tine and wherein said coupling comprises snap fitting said extension set to said catheter device.

17. The method of claim 15, wherein said decoupling comprises decoupling a latch of said catheter insertion device from a housing of said catheter device such that an internal portion of said latch is configured to release a spring within said catheter insertion device so that said spring urges a needle collet coupled to said needle to axially slide within said catheter insertion device to completely withdraw said needle through said catheter device and entirely into said catheter insertion device.

* * * * *